(12) United States Patent
Kostenis et al.

(10) Patent No.: US 7,794,927 B2
(45) Date of Patent: Sep. 14, 2010

(54) METHOD FOR IDENTIFYING AGONISTS OR ANTAGONISTS OF THE G-PROTEIN COUPLED RECEPTOR MAS-LIKE 1

(75) Inventors: Evi Kostenis, Grebenau (DE); Johann Gassenhuber, Weisbaden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 15 days.

(21) Appl. No.: 11/556,216

(22) Filed: Nov. 3, 2006

(65) Prior Publication Data

US 2007/0259378 A1 Nov. 8, 2007

Related U.S. Application Data

(62) Division of application No. 10/456,700, filed on Jun. 6, 2003, now abandoned.

(60) Provisional application No. 60/422,985, filed on Nov. 1, 2002.

(30) Foreign Application Priority Data

Jun. 8, 2002 (DE) ............................... 102 25 443

(51) Int. Cl.
*C12Q 1/00* (2006.01)
*C07K 14/435* (2006.01)
(52) U.S. Cl. .......................................... 435/5; 530/350
(58) Field of Classification Search ........................ None
See application file for complete search history.

(56) References Cited

U.S. PATENT DOCUMENTS

2003/0171293 A1    9/2003   Robas et al.

FOREIGN PATENT DOCUMENTS

| WO | WO 01/36471 | 5/2001 |
|----|-------------|--------|
| WO | WO 01/83555 | 11/2001 |
| WO | WO 01/98330 | 12/2001 |

OTHER PUBLICATIONS

Andrawis et al., Mas Oncogene Receptor Coupling and Peptide Specificity in Balb 3T3 and Vascular Smooth Muscle Cells, The American Journal of Medical Sciences, vol. 302, No. 6, pp. 329-334, 1991.

Whitehead et al., Membrane-Induced Secondary Structures of Neuropeptides: A Comparison of the Solution Conformations Adopted by Agonists and Antagonists of the Mammalian Tachykinin NK1 Receptor, Journal of Medicinal Chemistry, vol. 41, No. 9, Apr. 23, 1998, pp. 1497-1506.

Dong et al., A Diverse Family of GPCRs Expressed in Specific Subsets of Nociceptive Sensory Neurons, Cell, vol. 106, pp. 619-632, Sep. 7, 2001.

Robas et al., MrgX2 is a high potency cortistatin receptor expressed in dorsal root ganglion, J. Biol. Chem., vol. 278, 2003, pp. 44400-44404.

Yang et al., Adaptive evolution of MRGX2, a human sensory neuron specific gene involved in nociception, Gene, vol. 352, 2005, pp. 30-35.

Kamohara et al., Identification of MrgX2 as a human G-protein coupled-receptor for proadrenomedullin N-terminal peptides, Biochemical and Biophysical Research Communications, vol. 330, 2005, pp. 1146-1152.

*Primary Examiner*—Ruixiang Li

(57) ABSTRACT

The invention relates to a method for identifying a compound which stimulates or attenuates the activity of the G protein-coupled receptor mas-like 1.

6 Claims, No Drawings

METHOD FOR IDENTIFYING AGONISTS OR ANTAGONISTS OF THE G-PROTEIN COUPLED RECEPTOR MAS-LIKE 1

The present invention relates to a method for identifying a compound which modifies the activity of the G protein-coupled receptor mas-like 1.

G protein-coupled receptors mediate extracellular signals such as, for example, from hormones, neurotransmitters, light or odorants via G proteins into the interior of the cell, and various effects can be initiated via an intracellular signal cascade. G proteins normally consist of three different subunits (alpha, beta, gamma). Various heterodimeric G proteins which differ in receptor specificity and effect are known. The G proteins are activated by GTP. A well-known G protein is transducin from the vision process.

G protein-coupled receptors (GPCR) play an important part in a large number of physiological processes. They are one of the largest protein families known. It is currently estimated that about 1000 genes in the human genome code for this class of receptors. GPCR are membrane proteins with 7 transmembrane α-helices. A large number of medicaments displays its effect via GPCRs.

GPCRs are involved especially in signal processing and control of the organism and therefore play a superordinate part in maintaining the function of the intact organism.

The binding of an extracellular ligand leads to a conformational change in the relevant GPCR. The conformational change creates the preconditions for interaction with the respectively associated G protein. The G protein in turn initiates an intracellular signal cascade which is characteristic of the relevant cell type. The so-called second messengers are characteristic of intracellular signal cascades. By these are meant low molecular weight compounds such as, for example, cAMP (cyclic adenosine monophosphate), cGMP (cyclic guanosine monophosphate) or $Ca^{2+}$. The intracellular signaling is controlled by changes in the concentration of the second messengers. The G proteins and their subunits interact for this purpose with proteins such as adenylate cyclase, phospholipase C or ion channels. The change in the concentration of the second messenger in turn brings about an activation or inactivation of other proteins, especially of kinases and phosphatases. The signal finally terminates in a response typical of the particular cell assembly, for example the expression of a protein.

The heterotrimeric G proteins are located on the inside of the plasma membrane. An activated receptor makes contact with the G protein heterotrimer, which then dissociates an α subunit and the βγ complex. Both the activated α subunit and the βγ complex are able to influence intracellular effector proteins. The G protein α subunit family can be divided into various classes. Known examples are the Gαs, Gαi, Gαq and Gα12 classes. GPCRs are classified according to the activated G proteins.

GPCRs of the Gs class mediate, via activation of Gαs, the stimulation of adenylate cyclase and increase the intracellular cAMP concentration. GPCRs of the Gi class bring about, via activation of Gαi, an inhibition of adenylate cyclase and reduce the intracellular cAMP.

GPCRs of the Gq class in turn achieve, via activation of Gαq, a stimulation of various PLCβ isoforms and lead, via hydrolysis of membrane-bound phosphatidyl inositol 4,5-biphosphate, to diacylglycerol and inositol triphosphate (IP3). IP3 releases $Ca^{2+}$ from intracellular stores. Most GPCRs are able to make contact with only one G protein β subunit family, i.e. they have selectivity for a particular signal transduction pathway.

G proteins with altered receptor specificity and different attachment to a signal transduction pathway can be constructed by joining together components from different G proteins to give hybrid G proteins by the methods of molecular biology and biochemistry.

Hybrid G proteins are fusion constructs which combine within one protein sequences of different Gα subunits. Thus, for example, it is possible by fusing the receptor recognition region of Gαi with the effector activation region of Gαq to produce a Gαq/i hybrid which receives the signals of Gi-coupled receptors but switches on the Gαq PLCβ signal transduction pathway. Such a hybrid in which the C-terminal 5 amino acids of Gαq have been replaced by the corresponding Gαi sequence (Gαiq5) was described for the first time by Conklin et al. Nature 363, 274-276 (1993). This "rerouting" of receptors has the advantage that the assay endpoint (increase in intracellular $Ca^{2+}$ concentration compared with inhibition of adenylate cyclase) is more easily accessible by measurement techniques and can be used in high throughput screening.

Substance P is a neurotransmitter which is released both by central and by peripheral nerve endings of primary afferent neurons. The biological effects of substance P are mediated by tachykinin receptors (=neurokinin receptors) which belong to the group of G protein-coupled receptors. At present, three tachykinin receptors are known: NK1, NK2 and NK3. NK1 preferentially binds substance P, NK2 preferentially binds neurokinin A and NK3 preferentially binds neurokinin B. The endogenous tachykinins are, however, not particularly selective for the respective receptor subtypes and in principle substance P, NKA and NKB activate all three NK receptor subtypes. In addition to the known neurokinin receptor subtypes, a further subtype, the NK4 receptor, is postulated.

Substance P is thought to be associated with a large number of disorders in which chronic inflammation and pain are involved, such as, for example, asthma, chronic bronchitis, inflammatory gastrointestinal disorders, inflammation of the bladder, but also migraine, depression, vomiting and epileptic disorders. Substance P plays an important part not least in the cardiovascular area. Substance P is a very strong vasodilator. Vasodilatation and reduction of blood pressure are brought about via release of NO from the endothelium of large vessels (mediated by NK1 receptors). Substance P—acting via neurokinin receptors—is additionally an important mediator of neurogenic plasma extravasation: activation of NK1 receptors in endothelial cells of postcapillary venules makes the tight junctions (cell-cell contacts) permeable and thus permits plasma proteins to emerge from the vessel lumen into the interstitial space.

Whereas the role of the tachykinins (substance P, neurokinin A and neurokinin B) has been investigated reasonably well, little is known about the physiological and pathophysiological effects of substance P degradation products. Substance P is metabolized to N-terminal fragments (1-9,1-7,1-4) and to C-terminal fragments (2-11, 3-11). Whereas the effects of substance P cleavage products on the known neurokinin receptors have in some cases already been described, it is not at present known whether these cleavage products are also able themselves to bind to receptors and initiate a signal effect, that is to say act as natural ligands. A ligand means a molecule which reversibly binds to a G protein-coupled receptor and exerts via this binding an effect on the receptor (stabilization, inactivation, stimulation). This effect generally relates to a downstream intracellular signal cascade and can be detected from the effects on the signal cascade. A ligand is natural if it is produced by a biological system.

The nucleotide sequence and amino acid sequence of the G protein-coupled receptor mas-like 1 is known and available to the public (Genbank: AC 027026). The nucleotide sequence of mas-like 1 is reproduced in SEQ ID No. 1 and the amino acid sequence of mas-like 1 is reproduced in SEQ ID No. 2.

No natural ligand for the receptor mas-like 1 was previously known. The disadvantage of this was that no agonists or antagonists of this receptor were identifiable. Agonists and antagonists are very useful aids for studying the function of a receptor in relation to its normal activity or pathologically altered activity. Agonists and antagonists are furthermore advantageous in the restoration of pathologically altered receptor activities which may be manifested inter alia by abnormally reduced or increased activity. It is an object of the present invention accordingly to provide a method for identifying a compound which has an agonistic or antagonistic effect on the receptor mas-like 1.

The invention relates to a method for identifying a chemical compound which specifically binds to the G protein-coupled receptor mas-like 1, where a] at least one cell which expresses the receptor mas-like 1 on its surface is provided,
b] at least one chemical compound is provided,
c] the cells from a] are brought into contact with the chemical compound from b] under conditions making binding to the receptor possible,
d] the binding of the chemical compound to the receptor mas-like 1 is established.

Particularly important for producing conditions which make binding of a chemical compound to the receptor possible is the temperature or the pH. The selected temperature is preferably in the range from room temperature to 40° C., particularly preferably in the range from 36° C. to 38° C. and very particularly preferably 37° C. The pH is preferably in the range of values from 6 to 8 and particularly preferably at pH 7.0.

The invention further relates to a method for identifying a chemical compound which binds specifically to the G protein-coupled receptor mas-like 1, where a] a preparation of cells which express the receptor mas-like 1 on their surface, in which this receptor is present, is provided,
b] at least one chemical compound is provided,
c] the cells from a] are brought into contact with the chemical compound from b] under conditions making binding to the receptor possible,
d] the binding of the chemical compound to the receptor mas-like 1 is established.

In a preferred embodiment, the preparation of cells comprises the membrane fraction of a cell extract.

The invention also relates to a method for identifying a chemical compound which binds to the G protein-coupled receptor mas-like 1 in a specific manner and competitively in relation to a first chemical compound, where a] at least one cell which expresses said receptor mas-like 1 on its surface is provided,
b] at least one first chemical compound which binds to the receptor mas-like 1 is provided,
c] at least one second chemical compound which differs from the first chemical compound is provided,
d] the cells from a] are brought into contact with the first chemical compound from b] and the second chemical compound from c] either simultaneously or successively under conditions which make binding to the receptor possible,
e] binding of the first chemical compound to the receptor or binding of the second chemical compound to the receptor or binding of the first and second chemical compound to the receptor is determined.

In a preferred embodiment thereof, the first chemical compound consists of substance P or a cleavage product of substance P or the neuropeptide FF.

To determine the binding of the first chemical compound and/or the binding of the second chemical compound in the method described above and the other methods of this invention it may be necessary to construct a calibration plot.

The invention further relates to a method for identifying a chemical compound which binds to the G protein-coupled receptor mas-like 1 in a specific manner and competitively in relation to a first chemical compound, where a] a preparation of cells which express the receptor mas-like 1 on their surface, in which this receptor is present, is provided,
b] at least one first chemical compound which binds to the receptor mas-like 1 is provided,
c] at least one second chemical compound which differs from the first chemical compound is provided,
d] the cells from a] are brought into contact with the first chemical compound from b] and the second chemical compound from c] either simultaneously or successively under conditions which make binding to the receptor possible,
e] binding of the first chemical compound to the receptor or binding of the second chemical compound to the receptor or binding of the first and second chemical compound to the receptor is determined. In a preferred embodiment thereof, the preparation of cells comprises the membrane fraction of a cell extract. In a further preferred embodiment, the first chemical compound consists of substance P or a cleavage product of substance P or the neuropeptide FF.

The invention also relates to a method for identifying a chemical compound which specifically binds to and activates the G protein-coupled receptor mas-like 1, where a] at least one cell which expresses the receptor mas-like 1 on its surface and in which a second messenger signal cascade can be initiated by means of the receptor mas-like 1 is provided,
b] at least one chemical compound is provided,
c] the cells from a] are brought into contact with the chemical compound from b] under conditions which make binding to and activation of the receptor possible,
d] the change in the concentration of the second messenger in the cell is determined in the presence and absence of the chemical compound, with an alteration in the presence of the chemical compound indicating an activation of the receptor.

The invention further relates to a method for identifying a chemical compound which specifically binds to, and activates, the G protein-coupled receptor mas-like 1, where a] a preparation of cells which express the receptor mas-like 1 on their surface is provided, it being possible to initiate a second messenger signal cascade in this preparation,
b] at least one chemical compound is provided,
c] the preparation of cells from a] is brought into contact with the chemical compound from b] under conditions which make binding to, and activation of, the receptor possible,
d] the change in the concentration of the second messenger in the preparation of the cell is determined in the presence and absence of the chemical compound, with an alteration in the presence of the chemical compound indicating an activation of the receptor mas-like 1.

In a preferred embodiment thereof, the preparation of cells comprises the membrane fraction of a cell extract.

The invention additionally relates to a method for identifying a chemical compound which specifically binds to, and inhibits, the G protein-coupled receptor mas-like 1, where a] at least one cell which expresses the receptor mas-like 1 on its surface and in which a second messenger signal cascade can be initiated by means of the receptor mas-like 1 is provided,
b] at least one chemical compound is provided,
c] the cells from a] are brought into contact with the chemical compound from b] under conditions which make binding to and inactivation of the receptor possible,
d] the change in the concentration of the second messenger in the cell is determined in the presence and absence of the chemical compound, with an alteration in the presence of the chemical compound indicating an inactivation of the receptor mas-like 1.

The invention further relates to a process for identifying a chemical compound which specifically binds to, and inhibits, the G protein-coupled receptor mas-like 1, where a] a preparation of cells which express the receptor mas-like 1 on their surface is provided, it being possible to initiate a second messenger signal cascade in this preparation,
b] at least one chemical compound is provided,
c] the preparation of cells from a] is brought into contact with the chemical compound from b] under conditions which make binding to, and inactivation of, the receptor possible,
d] the change in the concentration of the second messenger in the preparation of the cell is determined in the presence and absence of the chemical compound, with an alteration in the presence of the chemical compound indicating an inactivation of the receptor mas-like 1.

In a preferred embodiment thereof, the preparation of cells comprises the membrane fraction of a cell extract.

The invention also relates to a pharmaceutical preparation comprising a compound which has been identified by one of the methods described above, and in addition excipients for formulating a medicament.

In a preferred embodiment, the pharmaceutical preparation comprises substance P or a cleavage product of substance P.

The invention further encompasses the use of substance P or of a cleavage product of substance P or of neuropeptide FF for producing a medicament for the treatment of a disease caused by a dysfunction of the receptor mas-like 1.

The invention further relates to the use of a compound which has been identified by a method of the invention for producing a complex of the receptor mas-like 1 with this compound. Suitable compounds for producing such a complex are, for example, substance P, a cleavage product of substance P or neuropeptide FF. The invention also relates to a complex of the receptor mas-like 1 and substance P, a cleavage product of substance P or neuropeptide FF. A complex means in this connection a compound composed of one or more proteins of the receptor in at least specific binding with substance P, a cleavage product of substance P or neuropeptide FF and possible membrane constituents or detergents to stabilize the receptor or receptor/ligand complex. The binding is specific when the binding constant is less than or equal to 100 µM.

The natural ligand may already be present in the biological material or the preparation of biological material. However, such a ligand can also be added from outside. For this purpose, the ligand should be present in an amount, concentration and degree of purity such that its binding to receptor and initiation of the receptor signal is brought about.

Addition of the natural ligand takes place after the biological material or a preparation of the biological material, each of which contain the G protein-coupled receptor mas-like 1, is available in a suitable way (preparation/amount).

Such a natural ligand is preferably substance P, a cleavage product of substance P, or neuropeptide FF. The natural ligands and, in particular, also substance P, a cleavage product of substance P or neuropeptide FF may, for use in the method of the invention, comprise a label which can be detected by a suitable detection method. Such a label is, for example, a radioactive label or a fluorometrically detectable label.

The method of the invention is preferably used in such a way that the identified compounds act agonistically or antagonistically toward the natural ligand.

The invention also relates to a compound which modifies the activity of the G protein-coupled receptor mas-like 1, where the compound has been identified by a method as described above.

Such a compound is distinguished by having a mass preferably between 0.1 and 50 kDa, or particularly preferably between 0.1 and 5 kDa or very particularly preferably between 0.1 and 3 kDa.

Such a compound which has been identified by a method of the invention may be a protein, an amino acid, a polysaccharide, a sugar, a polynucleotide, a nucleotide, a fatty acid-containing compound, a fat, a fatty acid, a fatty acid derivative or an aromatic hydrocarbon compound.

The invention further relates to a medicament which comprises a compound which has been identified by a method of the invention, and additionally formulation excipients for a medicament and/or other additives. This medicament is particularly suitable for the treatment of a cardiovascular disorder.

A compound which has been identified by a method of the invention may be used to produce a medicament for treating a cardiovascular disorder.

The G protein-coupled receptor mas-like 1 for carrying out the method of the invention can be produced by expression of an exogenous DNA sequence in a prokaryote or eukaryote. Suitable in principle for producing the protein is any prokaryotic or eukaryotic plasmid vector, bacteriophage vector or yeast plasmid vector. Examples of such vectors are pBR322, pUC18,19, pBluescript, pcDNA3.1 and others. The expression can take place transiently or permanently.

Recombinant vector constructions can be produced with the assistance of relevant expert knowledge as described, for example, in "F. M. Ausubel et al., Current Protocols in Molecular Biology, Wiley & Sons, New York (ISBN 0-471-50338-X)" or in "J. Sambrook, E. F. Fritsch, T. Maniatis, Molecular Cloning, second edition, Cold Spring Harbor Laboratory Press" (ISBN 0-87969-309-6). This entails a polynucleotide coding for an amino acid sequence as shown in one of the sequence descriptions (SEQ ID NO. 1) or a polynucleotide sequence as shown in one of the sequence descriptions (SEQ ID NO. 2) being incorporated into a basic vector. Basic vector is intended to mean a vector into which a polynucleotide sequence of a polynucleotide can be incorporated by the methods of molecular biology and can be cloned in a microorganism, for example a bacterium, fungus or the cell of a cell culture. The basic vector may consist for example of a plasmid having an antibiotic resistance marker, an origin of replication suitable for replication of the plasmid in bacteria or cell cultures, and a promoter suitable for expression of a protein. The basic vector may also consist for example of a phage vector, a phagemid vector, a phasmid vector, a cosmid vector, a virus vector, a YAC vector or other vector type. Examples of basic vectors are pUC 18, pUC19, pBluescript, pKS, pSK and others. Incorporation of the polynucleotide which is to be incorporated takes place via suitable restriction cleavage sites using the appropriate restriction enzymes which are commercially available from companies such as BioLabs, Roche Diagnostics, Stratagene and others. Such restriction cleavage sites may be, for example, the recognition sites of the restriction enzymes BamHI, EcoRI, SalI, EcoRV and others.

The recombinant vector construction consists in a preferred embodiment of an expression vector which can be used in eukaryotes and/or prokaryotes. An expression vector comprises a promoter which can be functionally connected to a polynucleotide sequence so that a protein encoded by this polynucleotide sequence is synthesized in a biological organism, for example a bacterium, fungus or the cell of a eukaryotic cell line. The promoter may be inducible for example by tryptophan or in a constitutive activity. Examples of expression vectors are pUC18, pUC19, pBluescript, pcDNA3.1 or others.

Biological material is any material which contains genetic information and can itself reproduce or be reproduced in a biological system. Examples of biological material are cells from human or animal tissues or organs such as, in particular, brain, adipose tissue, lung, heart, liver, kidney, spleen, muscle or others. Examples of biological material are also bacteria or fungi such as, for example, *Escherichia coli* or *Saccharomyces cerevisiae*. Biological material also encompasses cells from cell cultures.

Biological material can be obtained in the case of cells from animal or human tissues by biopsy, surgical removal, removal by means of syringes or catheters or comparable techniques. The cells removed in this way can be deep-frozen, worked up or put in cell culture. Bacteria and yeast cells are grown and worked up using conventional techniques of microbiology.

The skilled worker will find appropriate instructions therefor in "Current Protocols in Molecular Biology; ed.: F. M. Ausubel et al., continually revised, 2001 edition, published by John Wiley & Sons".

Biological material may also consist of cells of an animal cell culture. Examples of such cells are mouse cells, rat cells or hamster cells. The cell culture cells may be primary cell types or established cell lines. Examples of established cell lines are mouse 3T3 cells, CHO cells, HEK cells or Hela cells. The maintenance, culturing and growing of cell lines is described in standard textbooks such as, for example, in "Basic Cell Culture; ed.: J. M. Davis IRL Press, Oxford (1996)".

A preparation of a biological material is produced for example by disruption of the biological material and subsequent purification steps. Methods for disruption of the biological material may be in particular repeated freezing and thawing, treatment with ultrasound, the use of a French press, addition of detergents and enzymes or similar. Subsequent purification steps consist, for example, of differential centrifugation, precipitation with ammonium sulfate or organic solvents, use of chromatographic techniques and others. Chromatographic techniques are, for example, polyacrylamide gel electrophoresis, high pressure liquid chromatography, ion exchange chromatography, affinity chromatography, gas chromatography, mass spectrometry and others. For this, and in particular also for detailed instructions for the purification of proteins, detailed instructions are available to the skilled worker in textbooks such as, in particular, in "Current Protocols in Protein Science, ed.: J. E. Coligan et al., 2001 edition, published by John Wiley & Sons".

The biological material or the preparation of biological material can be brought into contact with a chemical compound in conventional laboratory vessels such as, for example, Eppendorf vessels, centrifuge tubes or glass flasks. The underlying aqueous medium comprises, for example, buffer substances, nutrient constituents, singly charged or doubly charged ions such as $Na^+$, $K^+$, $Ca^{2+}$, $Cl^-$, $SO_4^{2-}$, $PO_3^{2-}$ or others, also proteins, glycerol or others. Particular constant conditions such as, in particular, the temperature, the pH, the ionic conditions, the concentration of a protein, the volume or other factors may be advantageous for the bringing into contact. This is achieved by, for example, carrying out the bringing into contact in incubation apparatuses kept at a constant temperature, in the presence of a buffer or with the previously accurately weighed amounts of the ions or proteins. The aqueous solvent may in particular also comprise a certain proportion of an organic solvent such as dimethyl sulfoxide, methanol or ethanol. The content of such a solvent is, however, preferably not more than 10% by volume of the mixture.

The provision of a chemical compound takes place for example by chemical synthesis. The skilled worker is familiar with standard methods of synthesis. The chemical compound may be part of a collection of chemical compounds like those produced by storage and cataloging of the chemical compounds from closed synthesis programs (called chemical libraries). The compound may in other cases have been produced by a microorganism, in particular a bacterium, but also by a fungus or a plant (natural product).

Suitable pharmaceutical compounds can be administered as medicaments in oral, peroral, topical, parenteral or rectal form. The mode of administration which is most suitable depends in each individual case on the nature and severity of the condition to be treated and on the type of compound used in each case. A suitable active ingredient concentration is about 1% to 35%, preferably about 3% to 15%.

EXAMPLES

Cloning of the Human mas-Like 1 Receptor

The sequence of the human GPCR mas-like 1 is deposited in databases accessible to the public. The corresponding Genbank accession number is AC 027026. SEQ ID No. 1 contains the nucleotide sequence of the mas-like 1 receptor. SEQ ID No. 2 shows the corresponding amino acid sequence. The human gene contains no introns. The receptor has therefore been amplified starting from genomic DNA using a polymerase chain reaction (PCR). The human genomic DNA was derived in the present case from Clontech, Palo Alto. Human genomic DNA from another company or produced oneself is also suitable in principle for carrying out the PCR. The PCR reaction conditions were chosen as follows: initial incubation at 94° C. for 10 min, then 35 cycles incubating at 94° C. for 1 min per cycle, then at 60° C. for 1 min, and finally at 72° C. for 2 min. The reaction was carried out using the GC-Melt Kit from Clontech. However, another protocol used in textbooks is also suitable for carrying out the PCR, in particular in relation to buffer conditions and enzyme. The primers used, as shown in SEQ ID No. 3 and 4, were constructed so that a HindIII site (SEQ ID No. 3) or an EcoRI cleavage site (SEQ ID No. 4) was present. The product formed in the PCR had a length of 1 260 base pairs. It was incorporated into the expression vector pcDNA3.1 by means of the HindIII and EcoRI cleavage sites. This vector is commercially available inter alia from Invitrogen, Carlsbad, Calif., USA.

Quantitative RT-PCR (Reverse Transcriptase Polymerase Chain Reaction) in Real Time Using TaqMan Commercially available RNA samples from the following tissues and organs were available: adrenal gland, fetal brain, fetal liver, small intestine, heart, kidney, liver, lung, pancreas, placenta, prostate, skeletal muscle, spleen, testes, thymus, bone marrow, salivary gland, thymus gland, trachea and uterus.

The RNA samples were initially subjected to a DNase digestion under standard reaction conditions. cDNA was produced from about 2 μg of the DNase-RNA with the aid of a reverse transcriptase from MMLV Moloney murine leukemia virus. The reaction mixture for this was adjusted to a pH of 7.0 and contained 25 mM $MgCl_2$, in each case 10 mM dNTPs, 50 μM random hexamer primer, 50 μM oligo(dT)$_{16}$ and 20 U/μl RNase inhibitor. The reaction was carried out in a volume of 100 μl, incubating first at 25° C. for 10 min and subsequently at 42° C. for 60 min, then inactivating at 95° C. for 5 min and finally cooling in ice.

The subsequent PCR was carried out using a TaqMan Universal PCR Master Mix from Applera, Weiterstadt, Germany. This corresponds in terms of the buffer, enzyme provision and other reagents to the customary laboratory protocols known to the skilled worker.

The following sequences were used as primers:

```
5'-TGC TTT GTG GCA AGG AGA CC-3'
(SEQ ID No. 5; "forward" primer)

5'-TTC CTA CCA GCC CGA CCA G-3'
(SEQ ID No. 6; "reverse" primer).
```

The incubation conditions for the PCR were chosen as follows: 2 min at 50° C., then 10 min at 95° C., subsequently 40 cycles at 95° C. for 15 seconds for each cycle and 1 min at 60° C. The primers were employed in a concentration each of 50 μM. Ribosomal 18 S RNA was used as control.

The quantitative analysis took place by means of fluorescence resonance energy transfer (FRET). The skilled worker knows the quantitative determination of this type also under the name Taqman PCR. A Taqman sample consists of a single-stranded oligonucleotide which is labeled on the ends with two different fluorophores. The fluorophore at the 3' end, called the acceptor, functions with an attenuating effect ("quencher") of the fluorophore at the 5' end, called the donor.

The donor at the 5' end is liberated through the 5'-exonuclease activity of the Taq DNA polymerase during the chain-extension reaction. Since the donor is no longer quenched in free form, the amount thereof can be determined using a fluorimeter. Since the amount of donor formed and the accumulated PCR product show a proportional relationship it is possible to quantify the amplified DNA. Care must always be taken that the melting temperature of the TaqMan sample is higher than that of the primers for the amplification.

The fluorophores used were FAM (6-carboxyfluorescein) as donor and TAMRA (5-carboxytetramethylrhodamine) as acceptor (=quencher).

The TaqMan sample used had the following nucleotide sequence:

```
                                        (SEQ ID. No. 7)
3'-TGA TCC CGG TCT TCC TGA TCC TTT TCA-5'.
```

Cell Culture and Transfection for the FLIPR Assay

CHO-K1 cells were cultivated in basal Iscove's medium supplemented with 10% fetal bovine serum, 10 000 U/ml-10 000 μg/ml penicillin-streptomycin, gentamycin and 2 mM glutamine.

Iscove's medium is commercially available inter alia from Biochrom, Berlin. The composition of Iscove's medium is described in "Iscove, N. N., Melchers, F., Journal of Experimental Medicine 147, 923-933 (1978)". The CHO-K1 cells were applied in an amount of $2 \times 10^5$ cells to a 35 mm culture dish for the transient transfection. The cells were transfected after incubation for about 24 hours or at a confluence of 50-80% with 2 μg of DNA using Lipofectamine reagent which is commercially available inter alia from Invitrogen Life Technologies, Karlsruhe.

About 16 to 18 hours after the transfection, the cells were transferred into 96-well microtiter plates with a density of about 80 000 cells per well. Incubation was then continued for 18 to 24 hours. After this, 95 μl of HBSS (Hank's buffered saline solution) which contained 20 mM HEPES, 2.5 mM probenecid, 4 μM Fluo4 and 1% fetal bovine serum were added, and incubation was carried out in the presence of 5% $CO_2$ at 37° C. for 1 hour. Fluo4 is a dye which fluoresces in the presence of $Ca^{2+}$. Fluo4 is sold commercially inter alia by Molecular Probes Europe BV, Leiden. After the incubation, the cells were washed three times with PBS (phosphate buffered saline) which contained 1 mM $MgCl_2$, 1 mM EDTA and 2.5 mM probenecid.

After the last washing step, about 100 μl of the solution were left on the cells in each well. The peptides to be tested were dissolved in water or DMSO (dimethyl sulfoxide) in a concentration of 2 mM. The appropriate dilutions of the final concentration (20 mM) were prepared starting from such a stock solution. The fluorescence was measured using a FLIPR (Fluorometric Imaging Plate Reader; Molecular Devices GmbH, Ismaning) for a total of 3 minutes at 1-second intervals for the first minute and at 3-second intervals during the second and third minute. The measurements between 18 seconds and 37 seconds were used to determine the agonistic effect.

Identification of Ligands of the Receptor mas-Like 1

Various peptides were tested for their property of stimulating the G protein-coupled receptor mas-like 1. The test was carried out using FLIPR technology. The receptor was for this purpose transiently expressed in CHO-K1 cells.

The following peptides were tested: neuropeptide FF, neuropeptide AF, neuropeptide SF, angiotensin, bradykinin, bombesin, adrenomedullin, substance P, substance P1-9, substance P2-11.

It was possible to detect the formation of fluorescence in the cells in the presence of substance P (ca. 500 fluorescence intensity units), substance P2-11 (ca. 2 500 fluorescence intensity units) and neuropeptide FF (ca. 2 000 fluorescence intensity units). The zero value was in each case about 20 fluorescence intensity units. Activation of the receptors showed a linear dependence in the concentration range from $5 \times 10^{-6}$ to $1 \times 10^{-5}$ M of substance P and substance P2-11. The $EC_{50}$ for substance P was 10.37 μM.

Substance P2-11 liberated arachidonic acid in the transiently transfected CHO-K1 cells.

It was thus possible to identify substance P, substance P2-11 and neuropeptide FF as natural ligands of the G protein-coupled receptor called mas-like 1. A test system for finding agonists and antagonists in relation to the activity of mas-like 1 which is designed in accordance with the detection method additionally contained substance P, substance P2-11 or Neuropeptide FF. Agonistic effects were shown inter alia by other fragments of substance P such as, for example, substance P4-11 (SEQ ID NO:11) or substance P1-9 (SEQ ID NO:12).

Neuropeptide FF has the following amino acid sequence:

```
                                        (SEQ ID No. 8)
    H-Phe-Leu-Phe-Gln-Pro-Gln-Arg-Pro-NH2.
```

Substance P2-11 has the following amino acid sequence:

```
                                        (SEQ ID No. 10)
Pro-Lys-Pro-Gln-Gln-Phe-Phe-Gly-Leu-Met.
```

The invention claimed is:

1. A method for identifying an agonist of the G protein-coupled receptor mas-like 1 having the amino acid sequence of SEQ ID NO: 2 comprising the steps of:
   a) providing at least one cell or membrane fraction of said cell which expresses said mas-like 1 receptor on its surface,
   b) providing at least one candidate chemical compound;
   c) providing at least one natural ligand of the GPCR mas-like 1 selected from the group consisting of substance P2-11 (SEQ ID NO:10), P4-11 (SEQ ID NO:11) and P1-9 (SEQ ID NO:12);
   d) contacting the at least one cell or membrane fraction with the at least one natural ligand to form a mixture and measuring a first activation of the GPCR mas-like 1;
   e) contacting the mixture with the at least one chemical compound;
   f) measuring a second activation of the GPCR mas-like 1; and
   g) comparing the first activation with the second activation, such that the second activation is greater than the first activation is indicative that the at least one chemical compound is an agonist the GPCR mas-like 1.

2. The method of claim 1 wherein said cell is selected from a group consisting of: CHO cells, CHO K1 cells, and HEK cells.

3. The method of claim 1, wherein the first and second activations are measured by measuring $[Ca^{2+}]$ in the mixture.

4. A method for identifying an antagonist of the G protein-coupled receptor mas-like 1 having the amino acid sequence of SEQ ID NO: 2 comprising the steps of:
   a) providing at least one cell or membrane fraction of said cell which expresses said mas-like 1 receptor on its surface,
   b) providing at least one candidate chemical compound;
   c) providing at least one natural ligand of the GPCR mas-like 1 selected from the group consisting of substance P2-11 (SEQ ID NO:10), P4-11 (SEQ ID NO:11) and P1-9 (SEQ ID NO:12);
   d) contacting the at least one cell or membrane fraction with the at least one natural ligand to form a mixture and measuring a first activation of the mas-like 1 receptor;
   e) contacting the mixture with the at least one chemical compound;
   f) measuring a second activation of the mas-like 1 receptor; and
   g) comparing the first activation with the second activation, such that the second activation is less than the first activation is indicative that the at least one chemical compound is an antagonist the GPCR mas-like 1.

5. The method of claim 4 wherein said cell is selected from a group consisting of: CHO cells, CHO K1 cells, and HEK cells.

6. The method of claim 4, wherein the first and second activations are measured by measuring $[Ca^{2+}]$ in the mixture.

* * * * *

SEQUENCE LISTING

<160> NUMBER OF SEQ ID NOS: 12

<210> SEQ ID NO 1
<211> LENGTH: 993
<212> TYPE: DNA
<213> ORGANISM: Homo sapiens

<400> SEQUENCE: 1

```
atggatccaa ccaccccggc ctggggaaca gaaagtacaa cagtgaatgg aaatgaccaa      60
gcccttcttc tgctttgtgg caaggagacc ctgatcccgg tcttcctgat ccttttcatt     120
gccctggtcg ggctggtagg aaacgggttt gtgctctggc tcctgggctt ccgcatgcgc     180
aggaacgcct tctctgtcta cgtcctcagc ctggccgggg ccgacttcct cttcctctgc     240
ttccagatta taaattgcct ggtgtacctc agtaacttct tctgttccat ctccatcaat     300
ttccctagct tcttcaccac tgtgatgacc tgtgcctacc ttgcaggcct gagcatgctg     360
agcaccgtca gcaccgagcg ctgcctgtcc gtcctgtggc ccatctggta cgctgccgc     420
cgccccagac acctgtcagc ggtcgtgtgt gtcctgctct gggccctgtc cctactgctg     480
agcatcttgg aagggaagtt ctgtggcttc ttatttagtg atggtgactc tggttggtgt     540
cagacatttg atttcatcac tgcagcgtgg ctgatttttt tattcatggt tctctgtggg     600
tccagtctgg ccctgctggt caggatcctc tgtggctcca ggggtctgcc actgaccagg     660
ctgtacctga ccatcctgct cacagtgctg gtgttcctcc tctgcggcct gcccttggc      720
attcagtggt tcctaatatt atggatctgg aaggattctg atgtcttatt ttgtcatatt     780
catccagttt cagttgtcct gtcatctctt aacagcagtg ccaacccat catttacttc      840
ttcgtgggct cttttaggaa gcagtggcgg ctgcagcagc cgatcctcaa gctggctctc     900
cagagggctc tgcaggacat tgctgaggtg gatcacagtg aaggatgctt ccgtcagggc     960
accccggaga tgtcgagaag cagtctggtg tag                                 993
```

<210> SEQ ID NO 2
<211> LENGTH: 330
<212> TYPE: PRT
<213> ORGANISM: Homo sapiens

<400> SEQUENCE: 2

```
Met Asp Pro Thr Thr Pro Ala Trp Gly Thr Glu Ser Thr Thr Val Asn
1               5                   10                  15

Gly Asn Asp Gln Ala Leu Leu Leu Cys Gly Lys Glu Thr Leu Ile
            20                  25                  30

Pro Val Phe Leu Ile Leu Phe Ile Ala Leu Val Gly Leu Val Gly Asn
        35                  40                  45

Gly Phe Val Leu Trp Leu Leu Gly Phe Arg Met Arg Arg Asn Ala Phe
    50                  55                  60

Ser Val Tyr Val Leu Ser Leu Ala Gly Ala Asp Phe Leu Phe Leu Cys
65                  70                  75                  80

Phe Gln Ile Ile Asn Cys Leu Val Tyr Leu Ser Asn Phe Phe Cys Ser
                85                  90                  95

Ile Ser Ile Asn Phe Pro Ser Phe Phe Thr Thr Val Met Thr Cys Ala
            100                 105                 110

Tyr Leu Ala Gly Leu Ser Met Leu Ser Thr Val Ser Thr Glu Arg Cys
        115                 120                 125

Leu Ser Val Leu Trp Pro Ile Trp Tyr Arg Cys Arg Arg Pro Arg His
```

-continued

```
            130                 135                 140
Leu Ser Ala Val Val Cys Val Leu Leu Trp Ala Leu Ser Leu Leu Leu
145                 150                 155                 160

Ser Ile Leu Glu Gly Lys Phe Cys Gly Phe Leu Phe Ser Asp Gly Asp
                165                 170                 175

Ser Gly Trp Cys Gln Thr Phe Asp Phe Ile Thr Ala Ala Trp Leu Ile
            180                 185                 190

Phe Leu Phe Met Val Leu Cys Gly Ser Ser Leu Ala Leu Leu Val Arg
        195                 200                 205

Ile Leu Cys Gly Ser Arg Gly Leu Pro Leu Thr Arg Leu Tyr Leu Thr
    210                 215                 220

Ile Leu Leu Thr Val Leu Val Phe Leu Leu Cys Gly Leu Pro Phe Gly
225                 230                 235                 240

Ile Gln Trp Phe Leu Ile Leu Trp Ile Trp Lys Asp Ser Asp Val Leu
                245                 250                 255

Phe Cys His Ile His Pro Val Ser Val Leu Ser Ser Leu Asn Ser
            260                 265                 270

Ser Ala Asn Pro Ile Ile Tyr Phe Phe Val Gly Ser Phe Arg Lys Gln
        275                 280                 285

Trp Arg Leu Gln Gln Pro Ile Leu Lys Leu Ala Leu Gln Arg Ala Leu
    290                 295                 300

Gln Asp Ile Ala Glu Val Asp His Ser Glu Gly Cys Phe Arg Gln Gly
305                 310                 315                 320

Thr Pro Glu Met Ser Arg Ser Ser Leu Val
                325                 330

<210> SEQ ID NO 3
<211> LENGTH: 24
<212> TYPE: DNA
<213> ORGANISM: Homo sapiens

<400> SEQUENCE: 3
aagcttatgg atccaaccac cccg                                       24

<210> SEQ ID NO 4
<211> LENGTH: 25
<212> TYPE: DNA
<213> ORGANISM: Homo sapiens

<400> SEQUENCE: 4
gaattctcaa gcccccatct cattg                                      25

<210> SEQ ID NO 5
<211> LENGTH: 20
<212> TYPE: DNA
<213> ORGANISM: Homo sapiens

<400> SEQUENCE: 5
tgctttgtgg caaggagacc                                            20

<210> SEQ ID NO 6
<211> LENGTH: 18
<212> TYPE: DNA
<213> ORGANISM: Homo sapiens

<400> SEQUENCE: 6
ttcctaccag cccgacca                                              18
```

```
<210> SEQ ID NO 7
<211> LENGTH: 27
<212> TYPE: DNA
<213> ORGANISM: Homo sapiens

<400> SEQUENCE: 7
tgatcccggt cttcctgatc cttttca                                              27

<210> SEQ ID NO 8
<211> LENGTH: 8
<212> TYPE: PRT
<213> ORGANISM: Homo sapiens

<400> SEQUENCE: 8

Phe Leu Phe Gln Pro Gln Arg Pro
1               5

<210> SEQ ID NO 9
<211> LENGTH: 11
<212> TYPE: PRT
<213> ORGANISM: Homo sapiens

<400> SEQUENCE: 9

Arg Pro Lys Pro Gln Gln Phe Phe Gly Leu Met
1               5                   10

<210> SEQ ID NO 10
<211> LENGTH: 10
<212> TYPE: PRT
<213> ORGANISM: Homo sapiens

<400> SEQUENCE: 10

Pro Lys Pro Gln Gln Phe Phe Gly Leu Met
1               5                   10

<210> SEQ ID NO 11
<211> LENGTH: 7
<212> TYPE: PRT
<213> ORGANISM: Homo sapiens

<400> SEQUENCE: 11

Pro Gln Gln Phe Phe Gly Leu
1               5

<210> SEQ ID NO 12
<211> LENGTH: 9
<212> TYPE: PRT
<213> ORGANISM: Homo sapiens

<400> SEQUENCE: 12

Arg Pro Lys Pro Gln Gln Phe Phe Gly
1               5
```